(12) United States Patent
Sato

(10) Patent No.: US 10,660,837 B2
(45) Date of Patent: May 26, 2020

(54) ORAL COMPOSITION AND ORAL PLAQUE DISPERSION AGENT

(71) Applicant: Kao Corporation, Chuo-ku, Tokyo (JP)

(72) Inventor: Tomoya Sato, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/325,264

(22) PCT Filed: Aug. 10, 2017

(86) PCT No.: PCT/JP2017/029029
§ 371 (c)(1),
(2) Date: Feb. 13, 2019

(87) PCT Pub. No.: WO2018/043086
PCT Pub. Date: Mar. 8, 2018

(65) Prior Publication Data
US 2019/0175474 A1   Jun. 13, 2019

(30) Foreign Application Priority Data

Aug. 31, 2016   (JP) .................................. 2016-168787

(51) Int. Cl.
*A61K 8/46*   (2006.01)
*A61Q 11/00*  (2006.01)
*A61K 8/34*   (2006.01)

(52) U.S. Cl.
CPC ................ *A61K 8/466* (2013.01); *A61K 8/34* (2013.01); *A61K 8/345* (2013.01); *A61K 8/46* (2013.01); *A61Q 11/00* (2013.01); *A61K 2800/5922* (2013.01); *A61K 2800/805* (2013.01)

(58) Field of Classification Search
CPC ..................................................... A61K 8/46
See application file for complete search history.

(56) References Cited

U.S. PATENT DOCUMENTS

| 3,420,875 | A |   | 1/1969  | Di Salvo et al. |
| 3,462,525 | A | * | 8/1969  | Levinsky ................ A61K 8/21 424/56 |
| 2014/0336409 | A1 |   | 11/2014 | Barnes et al. |
| 2015/0202134 | A1 |   | 7/2015  | Yoshikawa et al. |

FOREIGN PATENT DOCUMENTS

| EP | 0377261 A2      | 7/1990  |
| EP | 2952566 A1      | 12/2015 |
| JP | 2013-151474 A   | 8/2013  |
| JP | 2015-020970 A   | 2/2015  |
| JP | 2015-028123 A   | 2/2015  |
| JP | 2015-164904 A   | 9/2015  |
| JP | 2015-218151 A   | 12/2015 |
| JP | 2019-119729 A   | 7/2019  |
| JP | 2019-119730 A   | 7/2019  |
| WO | WO 2014/046301 A2 | 3/2014 |
| WO | WO 2015/140472 A1 | 9/2015 |
| WO | WO 2015/151915 A1 | 10/2015 |

OTHER PUBLICATIONS

International Search Report (ISR) for PCT/JP2017/029029; I.A. fd Aug. 10, 2017, dated Sep. 19, 2017 from the Japan Patent Office, Tokyo, Japan.
International Preliminary Report on Patentability (IPRP), Chapter I of the Patent Cooperation Treaty, including the Written Opinion for PCT/JP2017/029029; I.A. fd Aug. 10, 2017, dated Mar. 5, 2019, by the International Bureau of WIPO, Geneva, Switzerland.
Extended European Search Report (EESR) including the supplementary European search report and the European search opinion, for EP Application No. 17846095.2, dated Mar. 13, 2020, European Patent Office, Munich, Germany.
Database GNPD [Online] MINTEL: "Cool Mint Mouthwash," anonymous, Database accession No. 1394652, Sep. 1, 2010, retrieved from www.gnpd.com.

* cited by examiner

*Primary Examiner* — Benjamin J Packard
(74) *Attorney, Agent, or Firm* — Sterne, Kessler, Goldstein & Fox P.L.L.C.

(57) ABSTRACT

The present invention relates to an oral composition and an oral plaque dispersion agent that can effectively disperse plaque firmly adhered to a tooth surface by being applied to the oral cavity.
The oral composition comprises the following components (A), (B), and (C):
  (A) an olefin sulfonate having 14 or more and 20 or less carbon atoms;
  (B) a hydroxy alkane sulfonate having 14 or more and 20 or less carbon atoms; and
  (C) sorbitol,
  wherein the content of the component (A) is 3 mass % or more and 50 mass % or less based on the total content of the component (A) and the component (B).

17 Claims, No Drawings

ORAL COMPOSITION AND ORAL PLAQUE DISPERSION AGENT

FIELD OF THE INVENTION

The present invention relates to an oral composition and an oral plaque dispersion agent.

BACKGROUND OF THE INVENTION

Dental plaque (plaque) has been known as an aggregate of various bacteria present in the oral cavity, i.e., one type of so-called biofilm. Such plaque causes occurrence of stickiness and halitosis in the oral cavity and not only causes discomfort but also can cause dental caries, tartar, periodontal disease, and the like. In such circumstances, although various surfactants having detergency have been suitably used in agents and compositions for application to the oral cavity conventionally, still various developments have been performed for sufficiently enhancing an effect of removing plaque or biofilm.

For example, Patent Literature 1 discloses an oral biofilm-removing agent containing an α-olefin sulfonate, dextranase, and sugar alcohol, which gives good feeling upon use and moderate foaming and shows an excellent effect of chemically removing oral biofilm. Patent Literature 2 discloses an oral composition containing an α-olefin sulfonate having 14 carbon atoms, acylamino acid salt, and/or arginine, which improves an effect of removing oral biofilm while suppressing bitterness peculiar to anionic surfactants.

(Patent Literature 1) JP-A-2015-20970
(Patent Literature 2) JP-A-2013-151474

SUMMARY OF THE INVENTION

The present invention relates to an oral composition comprising the following components (A), (B), and (C):
(A) an olefin sulfonate having 14 or more and 20 or less carbon atoms;
(B) a hydroxy alkane sulfonate having 14 or more and 20 or less carbon atoms; and
(C) sorbitol,
wherein the content of the component (A) is 3 mass % or more and 50 mass % or less based on the total content of the component (A) and the component (B).

The present invention also relates to an oral plaque dispersion agent comprising the following components (A) and (B):
(A) an olefin sulfonate having 14 or more and 20 or less carbon atoms; and
(B) a hydroxy alkane sulfonate having 14 or more and 20 or less carbon atoms
as active components,
wherein the content of the component (A) is 3 mass % or more and 50 mass % or less based on the total content of the component (A) and the component (B).

In both the above-mentioned patent literatures, an α-olefin sulfonate, such as tetradecenesulfonate, is used. In such tetradecenesulfonate, at most about 20 mass % or less of hydroxyalkylsulfonate is merely included as a by-product, and there is still room for improvement in order to effectively disperse plaque firmly adhered to a tooth surface.

Accordingly, the present invention provides an oral composition and an oral plaque dispersion agent that can effectively disperse plaque firmly adhered to a tooth surface by being applied to the oral cavity.

The present inventor has accordingly conducted various studies and has found that an oral composition and an oral plaque dispersion agent that can effectively disperse plaque, even if the plaque is firmly adhered to a tooth surface, can be provided by using an olefin sulfonate generated from a raw material having a double bond in the main chain and a specific number of carbon atoms, so-called olefin, and a hydroxy alkane sulfonate generated in the generation of the olefin sulfonate as active components, in a specific quantitative relationship of these components such that a large amount of the hydroxyalkylsulfonate can be contained.

According to the oral composition of the present invention, application to the oral cavity can effectively disperse plaque firmly adhered to a tooth surface and can effectively accelerate removal of the plaque. The oral plaque dispersion agent of the present invention is a significantly useful agent that can effectively disperse plaque in the oral cavity.

DETAILED DESCRIPTION OF THE INVENTION

The present invention will now be described in detail.

The oral composition of the present invention contains an olefin sulfonate having 14 or more and 20 or less carbon atoms as a component (A) and a hydroxy alkane sulfonate having 14 or more and 20 or less carbon atoms as a component (B).

The olefin sulfonate as the component (A) is obtained using an olefin having a double bond in the main chain as a raw material and sulfonating the material, followed by neutralization and hydrolysis, and then purification. Meanwhile, the hydroxy alkane sulfonate as the component (B) is a hydroxy form of the component (A) and is a component generated in the generation of the component (A).

The number of carbon atoms of the olefin sulfonate as the component (A) is 14 or more, preferably 16 or more from the viewpoint of enhancing the plaque-dispersing effect. The number of carbon atoms of the olefin sulfonate as the component (A) is 20 or less, preferably 18 or less from the viewpoints of stability and productivity of the composition. These numbers of carbon atoms result from the olefin used as the raw material, and an olefin sulfonate of which the number of carbon atoms is other than above may be included depending on the raw material used.

The number of carbon atoms of the hydroxy alkane sulfonate as the component (B) is 14 or more, preferably 16 or more from the viewpoint of enhancing the plaque-dispersing effect. The number of carbon atoms of the hydroxy alkane sulfonate as the component (B) is 20 or less, preferably 18 or less from the viewpoints of stability and productivity of the composition. These numbers of carbon atoms result from the olefin used as the raw material (olefin raw material), and this olefin raw material may be different from the olefin raw material of the component (A), that is, the number of carbon atoms of the component (A) and the number of carbon atom of the component (B) may be different from each other.

In the oral composition of the present invention, the content of the component (A) is 3 mass % or more and 50 mass % or less based on the total content of the component (A) and the component (B). The present inventor has focused on the fact that the component (B), which has been conventionally treated as a mere by-product, is a useful component for effectively enhancing the plaque-dispersing effect, and the above-mentioned content of the component (A) increases the content of the hydroxy form as the component (B), preferably, to a level higher than the content of the olefin form as the component (A) to allow the plaque-dispersing effect to be dramatically enhanced.

The content of the component (A) is 50 mass % or less, preferably 45 mass % or less, more preferably 30 mass % or less, further preferably 25 mass % or less based on the total content of the component (A) and the component (B) from the viewpoint of effectively dispersing plaque firmly adhered to a tooth surface. In addition, the content of the component (A) is 3 mass % or more, preferably 5 mass % or more, more preferably 7 mass % or more, further preferably 9 mass % or more based on the total content of the component (A) and the component (B) from the viewpoints of the stability and productivity of the composition. The content of the component (A) is 3 mass % or more and 50 mass % or less, preferably form 5 to 50 mass %, more preferably from 7 to 45 mass %, further preferably from 9 to 30 mass %, further preferably from 9 to 25 mass % based on the total content of the component (A) and the component (B).

The content of the component (A) based on the total content of the component (A) and the component (B) can be measured with a high-performance liquid chromatography mass spectrometer (HPLC-MS). Specifically, the hydroxy form and the olefin form are separated from active components by HPLC and are then subjected to the MS to identify the component (A), and the content of the component (A) in the total content of the component (A) and the component (B) can be determined from the HPLC-MS peak areas. More specifically, the content can be measured using an HPLC apparatus "Agilent Technology 1100" (manufactured by Agilent Technologies Inc.) and a column "L-column ODS 4.6×150 mm" (manufactured by Chemicals Evaluation and Research Institute, Japan) under the following conditions:

Sample preparation: 1000-fold dilution with methanol, Eluent A: 10 mM ammonium acetate-containing water, Eluent B: 10 mM ammonium acetate-containing methanol, Gradient: 0 min (A/B=30%/70%)→10 min (30%/70%)→55 min (0%/100%)→65 min (0%/100%)→66 min (30%/70%)→75 min (30%/70%), MS apparatus: "Agilent Technology 1100 MS SL (G1946D)" (manufactured by Agilent Technologies Inc.), MS detection: anion detection m/z 60-1600, UV 240 nm.

Although the sulfonate group in the component (A) can be present at the 1-position or 2-position of the olefin chain as the main chain or further also inside the olefin chain, it is preferable that the component (A) contains an olefin sulfonate having a sulfonate group at the 2-position of the olefin chain from the viewpoint of enhancing the effect of dispersing plaque firmly adhered to a tooth surface. The sulfonate group in the component (B) is also the same and can be present at the 1-position or 2-position of the alkane chain as the main chain or further inside the alkane chain, but from the viewpoint of enhancing the effect of dispersing plaque firmly adhered to a tooth surface, it is preferable that the component (B) contains a hydroxy alkane sulfonate having a sulfonate group at the 2-position of the alkane chain.

Specifically, the total content of the olefin sulfonate having a sulfonate group at the 2-position of the olefin chain in the component (A) and the hydroxy alkane sulfonate having a sulfonate group at the 2-position of the alkane chain in the component (B) is preferably 5 mass % or more, more preferably 8 mass % or more, further preferably 10 mass % or more, further preferably 15 mass % or more based on the total content of the component (A) and the component (B) from the viewpoint of enhancing the effect of dispersing plaque firmly adhered to a tooth surface. In addition, the total content of the olefin sulfonate having a sulfonate group at the 2-position of the olefin chain in the component (A) and the hydroxy alkane sulfonate having a sulfonate group at the 2-position of the alkane chain in the component (B) is preferably 30 mass % or less, more preferably 25 mass % or less based on the total content of the component (A) and the component (B) from the viewpoint of, for example, productivity. The total content of the olefin sulfonate having a sulfonate group at the 2-position of the olefin chain in the component (A) and the hydroxy alkane sulfonate having a sulfonate group at the 2-position of the alkane chain in the component (B) is preferably from 5 to 30 mass %, more preferably from 8 to 30 mass %, further preferably from 10 to 25 mass %, further preferably from 15 to 25 mass % based on the total content of the component (A) and the component (B).

The total content of the olefin sulfonate having a sulfonate group at the 1-position of the olefin chain in the component (A) and the hydroxy alkane sulfonate having a sulfonate group at the 1-position of the alkane chain in the component (B) is preferably 1 mass % or more, more preferably 1.5 mass % or more, further preferably 2 mass % or more, further preferably 2.5 mass % or more based on the total content of the component (A) and the component (B) from the viewpoint of, for example, productivity. In addition, the total content of the olefin sulfonate having a sulfonate group at the 1-position of the olefin chain in the component (A) and the hydroxy alkane sulfonate having a sulfonate group at the 1-position of the alkane chain in the component (B) is preferably 20 mass % or less, more preferably 10 mass % or less, further preferably 5 mass % or less based on the total content of the component (A) and the component (B) from the viewpoint of enhancing the effect of dispersing plaque firmly adhered to a tooth surface. The total content of the olefin sulfonate having a sulfonate group at the 1-position of the olefin chain in the component (A) and the hydroxy alkane sulfonate having a sulfonate group at the 1-position of the alkane chain in the component (B) is preferably from 1 to 20 mass %, more preferably from 1.5 to 10 mass %, further preferably from 2 to 5 mass %, further preferably from 2.5 to 5 mass % based on the total content of the component (A) and the component (B).

The total content of the olefin sulfonate having a sulfonate group at the 1-position of the olefin chain in the component (A) and the hydroxy alkane sulfonate having a sulfonate group at the 1-position of the alkane chain in the component (B) or the total content of the olefin sulfonate having a sulfonate group at the 2-position of the olefin chain in the component (A) and the hydroxy alkane sulfonate having a sulfonate group at the 2-position of the alkane chain in the component (B) based on the total content of the component (A) and the component (B) can be determined from the peak area ratio of each component obtained by gas chromatography (GC).

Specifically, the components (A) and (B) were reacted with trimethylsilyl diazomethane and made into methylesterified derivatives, and each component was then separated by GC. The content of the internal olefin sulfonate having a sulfonate group at the 2-position is calculated using the peak area ratio of each component as the mass ratio. The apparatuses and the analytical conditions used in the measurement are as follows.

GC apparatus: "Agilent Technology 6850" (manufactured by Agilent Technologies Inc.), Column: "HP-1 capillary column" (30 m×320 μm×0.25 μm, manufactured by Agilent Technologies Inc.), Detector: hydrogen flame ionization detector (FID), Injection temperature: 300° C., Detector temperature: 300° C., He flow rate: 1.0 mL/min, Oven: 60° C. (0 min)→10° C./min→300° C. (10 min).

In the oral composition of the present invention, the total content of the component (A) and the component (B) as active components in the oral composition of the present invention is preferably 0.1 mass % or more, more preferably 0.2 mass % or more, further preferably 0.3 mass % or more, further preferably 0.4 mass % or more from the viewpoint of securing an excellent plaque-dispersing effect. In addition, the total content of the component (A) and the component (B) in the oral composition of the present invention is preferably 10 mass % or less, more preferably 8 mass % or less, further preferably 5 mass % or less from the viewpoint of retaining the good feeling upon use in application to the oral cavity. The total content of the component (A) and the component (B) in the oral composition of the present invention is preferably 0.1 mass % or more and 10 mass % or less, more preferably from 0.2 to 8 mass %, further preferably from 0.3 to 5 mass %, further preferably from 0.4 to 5 mass %.

The component (A) and the component (B) can be prepared through a process of sulfonating an olefin raw material having 14 or more and 20 or less carbon atoms, followed by neutralization, hydrolysis, and then purification of the resulting degradation product.

The sulfonation, neutralization, and hydrolysis may be performed under any conditions, and the conditions described in, for example, Japanese Patent No. 1633184 or 2625150, or Tenside Surf. Det. 31(5), 299, (1994) can be referred to. Although various methods can be used for purifying the degradation product obtained through the hydrolysis, it is preferable that the step for such purification includes a step of extracting the component (A) and the component (B) contained in an aqueous phase, which is carried out after addition of a nonpolar solvent and separation from an oil phase. That is, specifically, the step includes a step of dispersing the degradation product obtained by hydrolysis in ethanol and adding a nonpolar solvent thereto and a subsequent step of separating the oil phase, and further includes a step of extracting the component (A) and the component (B) from the separated aqueous phase. As the nonpolar solvent, one or more selected from, for example, petroleum ether, hexane, and toluene can be used. The step of separating the oil phase may be performed multiple times. Examples of the step of extracting the component (A) and the component (B) from the separated aqueous phase include a means of evaporating water and a means of removing precipitates in the aqueous phase.

The olefin raw material of the component (A) and the olefin raw material of the component (B) may be the same or different.

In the case of preparing the component (A) and the component (B) by sulfonating an olefin raw material, performing neutralization and hydrolysis, then adding a nonpolar solvent and separating the oil phase, and then extracting the components from the aqueous phase, the total content of an olefin having a double bond at the 2-position in the whole olefins as the raw material of the component (A) and the component (B) is preferably 10 mass % or more, more preferably 15 mass % or more, further preferably 20 mass % or more in total based on the total amount of the olefin raw material of the component (A) and the component (B) from the viewpoint of enhancing the plaque-dispersing effect. In addition, the total content of the olefins having a double bond at the 2-position in the olefin raw material of the component (A) and the component (B) is preferably 50 mass % or less, more preferably 45 mass % or less, further preferably 35 mass % or less in total based on the total amount of the olefin raw material of the component (A) and the component (B) from the viewpoints of reducing the production cost and improving the productivity.

In addition, from the viewpoints of further enhancing the plaque-dispersing effect and accelerating improvement of, for example, foaming property and foam quality, the content of an olefin having a double bond at the 1-position, i.e., an α-olefin, in the olefins as the raw material of the component (A) and the component (B) is preferably 5 mass % or less, more preferably 2 mass % or less; and preferably 0.1 mass % or more, preferably 0.2 mass % or more in total based on total amount of the olefin raw material of the component (A) and the component (B).

The distribution of double bonds in olefins as the raw material can be measured with, for example, a gas chromatograph-mass spectrometer (abbreviated to GC-MS). Specifically, olefins having different carbon chain lengths and the positions of the double bond are precisely separated into each component with a gas chromatograph analyzer (hereinafter, abbreviated to GC), the position of the double bond in each component can be identified with a mass spectrometer (hereinafter, abbreviated to MS) and the ratio of each component can be determined from the GC peak area.

The sulfonation reaction can be performed by reacting 1.0 to 1.2 mol sulfur trioxide gas with 1 mol olefin as the raw material. It is preferable to perform the reaction at a reaction temperature of 20° C. to 40° C. The neutralization is performed by reacting an alkaline aqueous solution of, for example, sodium hydroxide, ammonia, or 2-aminoethanol, in an amount of 1.0 to 1.5 molar times the theoretical value of the sulfonate group. The hydrolysis reaction may be performed in the presence of water at 90° C. to 200° C. for 30 minutes to 3 hours. These reactions can be continuously performed. After completion of the hydrolysis reaction, impurities are removed by extraction and the resultant is washed appropriately, to thereby purify the component (A) and the component (B). Although the purification can be performed by various methods, for example, a method by reduced-pressure distillation is preferred. In the reduced-pressure distillation, it is preferable to employ conditions of 120° C. to 180° C. and 0.1 to 10 mmHg.

The oral composition of the present invention contains sorbitol as a component (C). The composition for applying to the oral cavity containing such component (C) can secure the plaque-dispersing effect while securing the stability, enhance the effect of suppressing the discomfort due to the component (A) and the component (B) in the oral cavity, such as irritation of feeling of tingling and harmfulness, and produce good flavor. The content of the component (C) in the oral composition of the present invention is preferably 2 mass % or more, more preferably 4 mass % or more, and further preferably 5 mass % or more from the viewpoints of enhancing the effect of suppressing the discomfort and producing good flavor. In addition, the content of the component (C) in the oral composition of the present invention is preferably 60 mass % or less, more preferably 50 mass % or less, further preferably 40 mass % or less, further preferably 30 mass % or less from the viewpoints of providing fresh feeling upon use and flavor. Furthermore, when the oral composition of the present invention is a liquid oral composition, the content of the component (C) in the oral composition of the present invention is preferably 15 mass % or less, more preferably 10 mass % or less, further preferably 7 mass % or less. The content of the component (C) in the oral composition of the present invention is preferably from 2 to 60 mass %, more preferably from 4 to 50 mass %, further preferably from 5 to 40 mass %, further preferably from 5 to 30 mass %. Furthermore, when the oral composition of the present invention is a liquid oral composition, the content of the component (C) in the oral composition of the present invention is preferably from 2 to 15 mass %, more preferably from 4 to 10 mass %, further preferably from 4 to 7 mass %.

The oral composition of the present invention can contain a surfactant (D) other than the component (A) and the component (B). The surfactant as the component (D) may be, for example, one or more anionic surfactants selected from the group consisting of alkyl sulfate ester salts, acyl amino acid salts such as sodium acyl glutamate and sodium acyl sarcosinate, alkyl phosphates such as sodium alkyl phosphate, higher fatty acid sulfonated monoglyceride salts, fatty acid ester salts of isethionic acid, sodium N-methyl long-chain acyl taurates, and polyoxyethylene monoalkyl phosphates;

one or more nonionic surfactants selected from the group consisting of polyoxyethylene hydrogenated castor oils; sucrose fatty acid esters; sorbitan fatty acid esters; glycerol fatty acid esters such as monoglycerol stearate, decaglycerol monostearate, and pentaglycerol monomyristate; alkyl glycosides; polyglycerol fatty acid esters; polyoxyethylene monoalkyl (or alkenyl) ethers; polyoxyethylene-polyoxypropylene copolymers; polyoxyethylene alkylphenyl ethers such as polyoxyethylene nonylphenyl ether; amine oxide surfactants; fatty acid alkanolamides such as mono-(or di-) ethanolamide and coconut oil fatty acid diethanolamide; polyglycerol fatty acid esters such as decaglyceryl stearate and decaglyceryl laurate; and polyglycols such as polyethylene-polypropylene glycol; or one or more amphoteric surfactants selected from the group consisting of acetic acid betaine such as lauryldimethylaminoacetic acid betaine, imidazolinium betaine such as 2-alkyl-N-carboxymethyl-N-hydroxyethyl-N-imidazolium betaine, alkyl sulfobetaine such as lauryl sulfobetaine and lauryl hydroxysulfobetaine, coconut oil fatty acid amide alkyl betaine such as coconut oil fatty acid amide propyl betaine, and long-chain alkyl imidazoline betaine salts such as alkyl-1-hydroxyethylimidazoline betaine sodium.

Among them, the surfactant as the component (D) is preferably one or more selected from the group consisting of the anionic surfactants and nonionic surfactants other than the component (A) and the component (B), more preferably one or more anionic surfactants selected from the group consisting of sodium alkyl sulfate, sodium methyl lauroyl taurate, acyl glutamate, and acyl sarcosinate; or one or more nonionic surfactants selected from the group consisting of polyoxyethylene hydrogenated castor oils, sucrose fatty acid esters, polyglycerol fatty acid esters, and sorbitan fatty acid esters from the viewpoint of, for example, dispersibility of each component in the oral composition of the present invention, foaming ability, plaque-dispersing effect, or stability.

When the surfactant as the component (D) is an anionic surfactant (D1), the content of the component (D1) in the oral composition of the present invention is preferably 0.05 mass % or more, more preferably 0.1 mass % or more, and further preferably 0.2 mass % or more and preferably 1.5 mass % or less, more preferably 1.2 mass % or less, further preferably 1 mass % or less, and more further preferably 0.8 mass % or less as the total of the component (D1) from the viewpoints of securing foaming ability, plaque-dispersing effect, and balance between stability and suppression of harmfulness.

When the surfactant as the component (D) is a nonionic surfactant (D2), the content of the component (D2) in the oral composition of the present invention is preferably 0.1 mass % or more, more preferably 0.2 mass % or more, further preferably 0.3 mass % or more and preferably 2 mass % or less, more preferably 1.5 mass % or less, further preferably 1 mass % or less, further preferably 0.8 mass % or less as the total of the component (D2) from the viewpoints of enhancing the dispersibility of each component and improving stability, the viewpoint of sufficiently securing the plaque-dispersing effect, and the viewpoint of securing the balance between exhibition of these effects and securing of a good feeling upon use in application to the oral cavity.

When the oral composition of the present invention is, for example, a dentifrice composition such as toothpaste or powder dentifrice, the composition can contain a binder from the viewpoint of imparting an appropriate viscosity and enhancing the adhesiveness to a tooth surface to improve the plaque-dispersing effect. Specifically, the binder may be, for example, one or more selected from the group consisting of sodium arginate, sodium carboxymethylcellulose, carrageenan, xanthan gum, sodium polyacrylate, hydroxyethyl cellulose, hydroxypropyl cellulose, pectin, gum tragacanth, gum arabic, guar gum, karaya gum, locust bean gum, gellan gum, tamarind gum, *psyllium* seed gum, polyvinyl alcohol, sodium chondroitin sulfate, methoxyethylene-maleic anhydride copolymers, and the like. Among them, sodium carboxymethylcellulose, xanthan gum, and carrageenan are preferred. When the oral composition of the present invention is a liquid oral composition, the binder is preferably one or more selected from the group consisting of hydroxyethyl cellulose, hydroxypropyl cellulose, carrageenan, and xanthan gum.

The content of the binder in the oral composition of the present invention is preferably 0.2 mass % or more, more preferably 0.3 mass % or more, further preferably 0.5 mass % or more and preferably 2 mass % or less, more preferably 1.5 mass % or less from the viewpoints of achieving impartment of an appropriate viscosity and improvement of the plaque-dispersing effect with good balance.

When the oral composition of the present invention is, for example, a dentifrice composition such as toothpaste or powder dentifrice, the composition can further contain an abrasive from the viewpoints of enhancing the plaque-dispersing effect and effectively removing plaque. Examples of the abrasive include abrasive silica (oil absorption: 50 to 150 mL/100 g, wherein the oil absorption means the value measured based on the amount of boiled linseed oil absorbed in accordance with JIS K5101-13-2 (established in 2004)). The abrasive generally used has an RDA value (Radioactive Dentine Abrasion values, the value measured by ISO 11609 (established in 2010) a method for testing abrasability, protocol A) of 20 to 250. The content of the abrasive in the oral composition of the present invention is preferably from 5 to 20 mass %, more preferably from 8 to 15 mass %.

The oral composition of the present invention preferably contains a humectant selected from the group consisting of glycerol, propylene glycol, 1,3-butylene glycol, polyethylene glycol having a weight-average molecular weight of 800 or less, and dipropylene glycol from the viewpoint of obtaining a good feeling upon use. The content of the humectant in the oral composition of the present invention is preferably from 2 to 15 mass %, more preferably 4 to 10 mass %. In addition, from the viewpoints of obtaining an appropriate viscosity and a good feeling upon use, it is preferable to contain a thickening silica (the oil absorption measured based on the amount of boiled linseed oil absorbed in accordance with JIS K5101-13-2 (established in 2004) is from 200 to 400 mL/100 g). The content of the thickening silica in the oral composition of the present invention is preferably from 1 to 15 mass %, more preferably from 2 to 10 mass % from the viewpoints of an appropriate viscosity of the composition and the dispersibility of each component in the oral cavity.

The oral composition of the present invention can appropriately contain, in addition to the above-mentioned components, a foaming aid; a preservative such as isobutyl para-hydroxybenzoate, isopropyl parahydroxybenzoate, or ethyl parahydroxybenzoate; a pigment; a dye; a flavoring agent; and water such as purified water within a range that does not inhibit the effects of the present invention. The form of the oral composition of the present invention is not particularly limited and may be a dentifrice composition, such as toothpaste or powder dentifrice, or may be a liquid oral composition, such as mouthwash or liquid dentifrice.

Since, as described above, the oral composition of the present invention is excellent in the effect of enhancing the effect of dispersing plaque firmly adhered to a tooth surface, it is significantly effective as a composition for dispersing oral plaque or composition for removing oral plaque.

The oral plaque dispersion agent of the present invention comprises the following components (A) and (B):
(A) an olefin sulfonate having 14 or more and 20 or less carbon atoms; and
(B) a hydroxy alkane sulfonate having 14 or more and 20 or less carbon atoms as active components,
wherein the content of the component (A) is 3 mass % or more and 50 mass % or less based on the total content of the component (A) and the component (B).

In the oral plaque dispersion agent of the present invention, the contents of the component (A) and component (B) as the active components and the ratios thereof are synonymous with those of the component (A) and the component (B) in the above-described oral composition. The oral plaque dispersion agent of the present invention can exhibit an excellent plaque-dispersing effect in the oral cavity by these active components.

The oral plaque dispersion agent may further contain components other than the active components, the component (A) and the component (B), as needed, as in the oral composition.

The oral plaque dispersion agent of the present invention may be in a liquid form or may be in a gel or paste form.

With respect to the above-described embodiments of the present invention, the following oral composition and producing method thereof, composition for dispersing oral plaque, and oral plaque dispersion agent are further disclosed.

[1] An oral composition comprising the following components (A), (B), and (C):
(A) an olefin sulfonate having 14 or more and 20 or less carbon atoms;
(B) a hydroxy alkane sulfonate having 14 or more and 20 or less carbon atoms; and
(C) sorbitol,
wherein the content of the component (A) is 3 mass % or more and 50 mass % or less based on the total content of the component (A) and the component (B).

[2] The oral composition according to aspect [1], wherein the number of carbon atoms of the olefin sulfonate as the component (A) is preferably 16 or more and preferably 18 or less, and the number of carbon atoms of the hydroxy alkane sulfonate as the component (B) is preferably 16 or more and preferably 18 or less.

[3] The oral composition according to aspect [1] or [2], wherein the content of the component (A) is preferably 45 mass % or less, more preferably 30 mass % or less, further preferably 25 mass % or less and preferably 5 mass % or more, more preferably 7 mass % or more, further preferably 9 mass % or more based on the total content of the component (A) and the component (B).

[4] The oral composition according to any one of aspects [1] to [3], wherein the total content of an olefin sulfonate having a sulfonate group at the 2-position of the olefin chain in the component (A) and a hydroxy alkane sulfonate having a sulfonate group at the 2-position of the alkane chain in the component (B) is preferably 5 mass % or more, more preferably 8 mass % or more, further preferably 10 mass or more, further preferably 15 mass % or more and preferably 30 mass % or less, more preferably 25 mass % or less based on the total content of the component (A) and the component (B).

[5] The oral composition according to any one of aspects [1] to [4], wherein the total content of an olefin sulfonate having a sulfonate group at the 1-position of the olefin chain in the component (A) and a hydroxy alkane sulfonate having a sulfonate group at the 1-position of the alkane chain in the component (B) is preferably 1 mass % or more, more preferably 1.5 mass % or more, further preferably 2 mass % or more, more further preferably 2.5 mass % or more and preferably 20 mass % or less, more preferably 10 mass % or less, further preferably 5 mass % or less based on the total content of the component (A) and the component (B).

[6] The oral composition according to any one of aspects [1] to [5], wherein the total content of the component (A) and the component (B) in the oral composition of the present invention is preferably 0.1 mass % or more, more preferably 0.2 mass % or more, further preferably 0.3 mass % or more, further preferably 0.4 mass % or more and preferably 10 mass % or less, more preferably 8 mass % or less, further preferably 5 mass % or less.

[7] The oral composition according to any one of aspects [1] to [6], wherein the content of the component (C) in the oral composition of the present invention is preferably 2 mass % or more, more preferably 4 mass % or more, further preferably 5 mass % or more and preferably 60 mass % or less, more preferably 50 mass % or less, further preferably 40 mass % or less, more further preferably 30 mass % or less; and when the oral composition of the present invention is a liquid oral composition, the content is preferably 15 mass % or less, more preferably 10 mass % or less, further preferably 7 mass % or less.

[8] The oral composition according to any one of aspects [1] to [7], further comprising a surfactant (D) other than the component (A) and the component (B), wherein the component (D) is preferably one or more selected from the group consisting of anionic surfactants and nonionic surfactants other than the component (A) and the component (B), more preferably one or more anionic surfactants selected from the group consisting of sodium alkyl sulfate, sodium methyl lauroyl taurate, acyl glutamate, and acyl sarcosinate; or one or more nonionic surfactants selected from the group consisting of polyoxyethylene hydrogenated castor oils, sucrose fatty acid esters, polyglycerol fatty acid esters, and sorbitan fatty acid esters.

[9] The oral composition according to any one of aspects [1] to [8], wherein when the component (D) is an anionic surfactant (D1), the content of the component (D1) in the oral composition of the present invention is preferably 0.05 mass % or more, more preferably 0.1 mass % or more, further preferably 0.2 mass % or more and preferably 1.5 mass % or less, more preferably 1.2 mass % or less, further preferably 1 mass % or less, further preferably 0.8 mass % or less in total of the component (D1); and when the component (D) is a nonionic surfactant (D2), the content of the component (D2) in the oral composition of the present invention is preferably 0.1 mass % or more, more preferably 0.2 mass % or more, further preferably 0.3 mass % or more and preferably 2 mass % or less, more preferably 1.5 mass % or less, further preferably 1 mass % or less, more further preferably 0.8 mass % or less in total of the component (D2).

[10] The oral composition according to any one of aspects [1] to [9], which is a composition for dispersing oral plaque.

[11] An oral plaque dispersion agent comprising the following components (A) and (B):

(A) an olefin sulfonate having 14 or more and 20 or less carbon atoms; and (B) a hydroxy alkane sulfonate having 14 or more and 20 or less carbon atoms as active components, wherein the content of the component (A) is 3 mass % or more and 50 mass % or less based on the total content of the component (A) and the component (B).

[12] The oral plaque dispersion agent according to aspect [11], wherein the total content of an olefin sulfonate having a sulfonate group at the 2-position of the olefin chain in the component (A) and a hydroxy alkane sulfonate having a sulfonate group at the 2-position of the alkane chain in the component (B) is preferably 5 mass % or more, more preferably 8 mass % or more, further preferably 10 mass % or more, further preferably 15 mass % or more and preferably 30 mass % or less, more preferably 25 mass % or less based on the total content of the component (A) and the component (B).

[13] The oral plaque dispersion agent according to aspect [11] or [12], wherein the total content of an olefin sulfonate having a sulfonate group at the 1-position of the olefin chain in the component (A) and a hydroxy alkane sulfonate having a sulfonate group at the 1-position of the alkane chain in the component (B) is preferably 1 mass % or more, more preferably 1.5 mass % or more, further preferably 2 mass % or more, further preferably 2.5 mass % or more and preferably 20 mass % or less, more preferably 10 mass % or less, further preferably 5 mass % or less based on the total content of the component (A) and the component (B).

[14] The oral plaque dispersion agent according to any one of aspects [11] to [13], wherein the total content of the component (A) and the component (B) in the oral composition of the present invention is preferably 0.1 mass % or more, more preferably 0.2 mass % or more, further preferably 0.3 mass % or more, further preferably 0.4 mass % or more and preferably 10 mass % or less, more preferably 8 mass % or less, further preferably 5 mass % or less.

[15] The oral plaque dispersion agent according to any one of aspects [11] to [14], wherein the number of carbon atoms of the olefin sulfonate as the component (A) is preferably 16 or more and preferably 18 or less, and the number of carbon atoms of the hydroxy alkane sulfonate as the component (B) is preferably 16 or more and preferably 18 or less.

[16] The oral plaque dispersion agent according to any one of aspects [11] to [15], wherein the content of the component (A) is preferably 45 mass % or less, more preferably 30 mass % or less, further preferably 25 mass % or less and preferably 5 mass % or more, more preferably 7 mass % or more, further preferably 9 mass % or more based on the total content of the component (A) and the component (B).

[17] A method for producing the oral composition according to any one of aspects [1] to [9], comprising a step of preparing the component (A) and the component (B) through a step of sulfonating an olefin raw material having 14 or more and 20 or less carbon atoms (olefin to be used as a raw material of the component (A) and the component (B)), followed by neutralization, hydrolysis, and subsequent purification of the resulting degradation product.

[18] The method for producing the oral composition according to aspect [17], wherein the step of purification comprises a step of adding a nonpolar solvent to the degradation product obtained by the hydrolysis and a step of separating an oil phase thereafter, and further comprises a step of extracting the component (A) and the component (B) from an aqueous phase after the separation.

[19] The method for producing the oral composition according to aspect [18], wherein the step of adding a nonpolar solvent to the degradation product obtained by the hydrolysis is a step of dispersing the degradation product obtained by the hydrolysis in ethanol and then adding a nonpolar solvent thereto.

[20] The method for producing the oral composition according to aspect [18] or [19], wherein the nonpolar solvent is one or more selected from the group consisting of petroleum ether, hexane, and toluene.

[21] The method for producing the oral composition according to any one of aspects [18] to [20], wherein the total content of an olefin having a double bond at the 2-position in the whole olefins to be used as the raw material of the component (A) and the component (B) is preferably 10 mass % or more, more preferably 15 mass % or more, further preferably 20 mass % or more and preferably 50 mass % or less, more preferably 45 mass % or less, further preferably 35 mass % or less in total based on the total amount of the whole olefins to be used as the raw material of the component (A) and the component (B).

[22] The oral composition according to any one of aspects [1] to [9], which is a dentifrice composition that is toothpaste or powder dentifrice or a liquid oral composition that is mouthwash or liquid dentifrice.

[23] Use of the oral composition according to any one of aspects [1] to [9] for dispersing plaque adhered to a tooth surface.

[24] A method for dispersing plaque adhered to a tooth surface comprising applying the oral composition according to any one of aspects [1] to [9] to the oral cavity.

EXAMPLES

The present invention will now be specifically described based on Examples. The content of each component is represented by mass % unless otherwise specified in the tables.

Each physical property was based on the following methods.

«Method for Measuring Position of Double Bond of Olefin Raw Material»

The position of a double bond in an olefin raw material was measured by gas chromatography (hereinafter, abbreviated to GC). Specifically, the olefin raw material was reacted with dimethyl disulfide and was made into a dithiolate derivative, and each component was then separated by GC. The position of a double bond in the olefin raw material was determined from each peak area.

The apparatuses and the analytical conditions used in the measurement are as follows: GC apparatus (trade name: HP6890, manufactured by HEWLETT-PACKARD Company), Column (trade name: Ultra-Alloy-1HT capillary column, 30 m ×250 μm×0.15 μm, manufactured by Frontier Laboratories Ltd.), Detector (hydrogen flame ionization detector (FID)), Injection temperature: 300° C., Detector temperature: 350° C., He flow rate: 4.6 mL/min.

«Method for Measuring Content of Component (A) Based on Total Content of Component (A) (Olefin Form) and Component (B) (Hydroxy Form)»

The content of the component (A) was measured by HPLC-MS. Specifically, the hydroxy form and the olefin form were separated by HPLC, and the olefin form was identified through MS. The ratio of the olefin form was determined from the HPLC-MS peak area.

The apparatuses and the conditions used in the measurement are as follows: HPLC apparatus (trade name: Agilent Technology 1100, manufactured by Agilent Technologies Inc.), Column (trade name: L-column ODS, 4.6 ×150 mm, manufactured by Chemicals Evaluation and Research Institute, Japan), Sample preparation (1000-fold dilution with methanol), Eluent A (10 mM ammonium acetate-containing water), Eluent B (10 mM ammonium acetate-containing methanol), Gradient (0 min (A/B=30%/70%)→10 min (30%/70%)→55 min (0%/100%)→65 min (0%/100%)→66 min (30%/70%)→75 min (30%/70%)), MS apparatus (trade name: Agilent Technology 1100MS SL (G1946D)), MS detection (anion detection m/z 60-1600, UV 230 nm).

«Method for Measuring Content of Olefin Sulfonate Having Sulfonate Group at 2-Position»

The binding position of the sulfonate group was measured by GC. Specifically, an olefin sulfonate and a hydroxy alkane sulfonate were reacted with trimethylsilyl diazomethane and made into methylesterified derivatives, and each component was then separated by GC. The content of the olefin sulfonate having a sulfonate group at the 2-position was calculated using each peak area ratio as the mass ratio, and the content based on the total content of the component (A) and the component (B) was determined.

The apparatuses and the analytical conditions used in the measurement are as follows: GC apparatus (trade name: Agilent Technology 6850, manufactured by Agilent Technologies Inc.), Column (trade name: HP-1 capillary column, 30 m×320 μm×0.25 μm, manufactured by Agilent Technologies Inc.), Detector (hydrogen flame ionization detector (FID)), Injection temperature: 300° C., Detector temperature: 300° C., He flow rate: 1.0 mL/min, Oven (60° C. (0 min)→10° C./min→300° C. (10 min).

Production Example A: Synthesis of 30.4 Mass % of Olefin Raw Material Having 16 Carbon Atoms and Double Bond at 2-Position 1-Hexadecanol (product name: Kalcol 6098, manufactured by Kao Corporation, 7000 g (28.9 mol)) and a solid acid catalyst, γ-alumina, (STREM Chemicals, Inc., 700 g (10 mass % relative to the alcohol raw material)) were placed in a flask equipped with a stirrer and were reacted under stirring with circulating nitrogen (7000 mL/min) at 280° C. in the system for 3 hours. The alcohol conversion rate after completion of the reaction was 100%, and the purity of the olefin raw material having 16 carbon atoms (C16) was 99.6%. The resulting crude olefin raw material was transferred to a distillation flask and was distilled at 136° C. to 160° C. and 4.0 mmHg to obtain a purified C16 olefin raw material having an olefin purity of 100%. The double-bond distribution of the resulting olefin raw material was C1-position: 1.8 mass %, C2-position: 30.4 mass %, C3-position: 23.9 mass %, C4-position: 16.8 mass %, C5-position: 12.0 mass %, C6-position: 7.4 mass %, and C7- and C8-positions: 7.8 mass % in total.

Production Example B: Synthesis of 15.5 Mass % of Internal Olefin Having 16 Carbon Atoms and Double Bond at 2-Position 1-Hexadecanol (product name: Kalcol 6098, manufactured by Kao Corporation, 7000 g (28.9 mol)) and a solid acid catalyst, γ-alumina, (STREM Chemicals, Inc., 700 g (10 mass % relative to the alcohol raw material)) were placed in a flask equipped with a stirrer and were reacted under stirring with circulating nitrogen (7000 mL/min) at 280° C. in the system for 5 hours. The alcohol conversion rate after completion of the reaction was 100%, and the purity of the C16 internal olefin was 99.7%. The resulting crude internal olefin was transferred to a distillation flask and was distilled at 136° C. to 160° C. and 4.0 mmHg to obtain an internal olefin having 16 carbon atoms with an olefin purity of 100%. The double-bond distribution of the resulting internal olefin was C1-position: 0.9 mass %, C2-position: 15.5 mass %, C3-position: 14.0 mass %, C4-position: 16.7 mass %, C5-position: 16.2 mass %, C6-position: 15.6 mass %, and C7- and C8-positions: 21.2 mass % in total.

Production Example C: Synthesis of 31.3 Mass % of Olefin Raw Material Having 18 Carbon Atoms and Double Bond at 2-Position 1-Octadecanol (product name: Kalcol 8098, manufactured by Kao Corporation, 7000 g (25.9 mol)) and a solid acid catalyst, γ-alumina, (STREM Chemicals, Inc., 700 g (10 mass % relative to the alcohol raw material)) were placed in a flask equipped with a stirrer and were reacted under stirring with circulating nitrogen (7000 mL/min) at 280° C. in the system for 10 hours. The alcohol conversion rate after completion of the reaction was 100%, and the purity of the olefin raw material having 18 carbon atoms (C18) was 98.2%. The resulting crude olefin raw material was transferred to a distillation flask and was distilled at 148° C. to 158° C. and 0.5 mmHg to obtain a purified olefin raw material having an olefin purity of 100%. The double-bond distribution of the resulting olefin raw material was C1-position: 0.8 mass %, C2-position: 31.3 mass %, C3-position: 22.9 mass %, C4-position: 15.5 mass %, C5-position: 10.8 mass %, C6-position: 7.2 mass %, C7-position: 5.3 mass %, and C8- and C9-positions: 6.2 mass % in total.

Production Example D: Synthesis of 13.8 Mass % of Olefin Raw Material Having 18 Carbon Atoms and Double Bond at 2-Position 1-Octadecanol (product name: Kalcol 8098, manufactured by Kao Corporation, 7000 g (25.9 mol)) and a solid acid catalyst, γ-alumina, (STREM Chemicals, Inc., 700 g (10 mass % relative to the alcohol raw material)) were placed in a flask equipped with a stirrer and were reacted under stirring with circulating nitrogen (7000 mL/min) at 280° C. in the system for 13 hours. The alcohol conversion rate after completion of the reaction was 100%, and the purity of the olefin raw material having 18 carbon atoms (C18) was 98.5%. The resulting crude olefin raw material was transferred to a distillation flask and was distilled at 148° C. to 158° C. and 0.5 mmHg to obtain a purified olefin raw material having an olefin purity of 100%. The double-bond distribution of the resulting olefin raw material was C1-position: 0.8 mass %, C2-position: 13.8 mass %, C3-position: 12.4 mass %, C4-position: 14.8 mass %, C5-position: 14.2 mass %, C6-position: 13.1 mass %, C7-position: 12.1 mass %, and C8- and C9-positions: 18.6 mass % in total.

Production Example E: Synthesis of 31.8 Mass % of Olefin Raw Material Having 14 Carbon Atoms and Double Bond at 2-Position 1-Tetradecene (product name: Linealene 14, manufactured by Idemitsu Kosan Co., Ltd., 6000 g (26.7 mol)) and a solid acid catalyst, protonic β-zeolite, (CP-814E, Zeolyst International, Inc., 180 g (3 mass % relative to the α-olefin raw material)) were placed in a flask equipped with a stirrer and were reacted under stirring at 120° C. for 20 hours. Subsequently, the crude olefin raw material was transferred to a distillation flask and was distilled at 124° C. to 136° C. and 7.5 mmHg to obtain a purified olefin raw material having 14 carbon atoms (C14) with an olefin purity of 100%. The double-bond distribution of the resulting olefin raw material was C1-position: 1.3 mass %, C2-position: 31.8 mass %, C3-position: 23.8 mass %, C4-position: 21.0 mass %, C5-position: 8.6 mass %, and C6- and C7-positions: 13.6 mass % in total.

Production Example F: Synthesis of 27.8 Mass % of Olefin Raw Material Having 16/18 Carbon Atoms (Mass % Ratio: 79.4/20.6) and Double Bond at 2-Position An olefin raw material having 16 carbon atoms (C16) (the double-bond distribution was C1-position: 0.5 mass %, C2-position: 30.1 mass %, C3-position: 25.5 mass %, C4-position: 18.9 mass %, C5-position: 11.1 mass %, C6-position: 7.0 mass %, and C7- and C8-positions: 7.0 mass % in total) was prepared by the same method as in Production Example A except that the reaction time was adjusted.

An olefin raw material having 18 carbon atoms (C18) (the double-bond distribution was C1-position: 0.3 mass %, C2-position: 19.0 mass %, C3-position: 17.6 mass %, C4-position: 17.4 mass %, C5-position: 14.9 mass %, C6-position: 12.3 mass %, C7-position: 8.8 mass %, and C8- and C9-positions: 9.8 mass % in total) was prepared by the same method as in Production Example B except that the reaction time was adjusted.

11.9 kg of the resulting C16 olefin raw material and 3.1 kg of the resulting C18 olefin raw material were mixed to obtain 15.0 kg of C16/C18 (mass ratio: 79.4/20.6) olefin raw material. The double-bond distribution of this olefin raw material was C1-position: 0.4 mass %, C2-position: 27.8 mass %, C3-position: 23.9 mass %, C4-position: 18.6 mass %, C5-position: 11.9 mass %, C6-position: 8.1 mass %, C7-position: 4.6 mass %, C8-position: 3.8 mass %, and C9-position: 1.0 mass %.

Production Example I-1: Production of C16 Component (A) and Component (B)

The C16 olefin raw material (the content of the olefin raw material having a double bond at the 2-position was 30.4 mass %) prepared in Production Example A was sulfonated by means of sulfur trioxide gas using a thin-film sulfonation reactor equipped with an external jacket and allowing cooling water of 20° C. to pass through the external jacket of the reactor. The molar ratio of the SO₃ to the olefin raw material in the sulfonation reaction was set to 1.09. The resulting sulfonated product was added to an alkaline aqueous solution prepared with sodium hydroxide at an amount of 1.5 molar times the theoretical acid value, and neutralization was performed at 30° C. for 1 hour with stirring. The neutralized product was heated in an autoclave at 160° C. for 1 hour for hydrolysis to obtain a component (A) and a component (B) as a C16 crude product. Into a separatory funnel, 300 g of the crude product was transferred, 300 mL of ethanol was added thereto, and 300 mL of petroleum ether was then added at each time to remove oil-soluble impurities by extraction. On this occasion, inorganic compounds (the main component is mirabilite) precipitated at the oil/water interface by the addition of ethanol were also separated and removed from the aqueous phase by an oil/water separation procedure. This extraction and removal procedure was performed three times. Subsequently, the aqueous phase was evaporated to dryness to obtain C16 component (A) and component (B).

The content of the component (A) based on the total amount of the resulting component (A) and component (B) was 10 mass %. The content of the remaining olefin raw material in the total amount of the resulting component (A) and component (B) was less than 100 ppm (less than the minimum limit of detection of GC), and the content of inorganic compounds was 1.9 mass %. The total content of the olefin sulfonate having a sulfonate group at the 2-position and the hydroxy alkane sulfonate having a sulfonate group at the 2-position based on the total amount of the component (A) and the component (B) was 20.3 mass %.

Production Example I-2: Production of C16 Component (A) and Component (B)

C18 component (A) and component (B) were prepared from the C16 olefin raw material (the content of the olefin raw material having a double bond at the 2-position was 15.5 mass %) prepared in Production Example B under the same conditions as in Production Example I.

The content of the component (A) based on the total amount of the resulting component (A) and component (B) was 16 mass %. The content of the remaining olefin raw material in the total amount of the resulting component (A) and component (B) was less than 100 ppm (less than the minimum limit of detection of GC), and the content of inorganic compounds was 0.2 mass %. The total content of the olefin sulfonate having a sulfonate group at the 2-position and the hydroxy alkane sulfonate having a sulfonate group at the 2-position based on the total amount of the component (A) and the component (B) was 9.3 mass %.

Production Example I-3: Production of C16 Component (A) and Component (B)

The C16 olefin raw material (the content of the olefin raw material having a double bond at the 2-position was 30.1 mass %) prepared in Production Example A was sulfonated by means of sulfur trioxide gas using a thin-film sulfonation reactor equipped with an external jacket and allowing cooling water of 20° C. to pass through the external jacket of the reactor. The molar ratio of the SO₃ to the internal olefin in the sulfonation reaction was set to 1.09. The resulting sulfonated product was transferred to a round bottom flask, and heat aging was performed at 40° C. for 30 minutes with stirring. Subsequently, the resulting product was added to an alkaline aqueous solution prepared with sodium hydroxide at an amount of 1.5 molar times the theoretical acid value, and neutralization was performed at 30° C. for 1 hour with stirring. The neutralized product was heated in an autoclave at 160° C. for 1 hour for hydrolysis to obtain a component (A) and a component (B) as a C16 crude product. Into a separatory funnel, 300 g of the crude product was transferred, 300 mL of ethanol was added thereto, and 300 mL of petroleum ether was then added at each time to perform extraction. The extraction procedure was performed three times. The aqueous phase was evaporated to dryness to obtain C16 component (A) and component (B).

The content of the component (A) based on the total amount of the resulting component (A) and component (B) was 44 mass %. The content of the remaining olefin raw material in the total amount of the resulting component (A) and component (B) was less than 100 ppm (less than the minimum limit of detection of GC), and the content of inorganic compounds was 1.0 mass %. The total content of the olefin sulfonate having a sulfonate group at the 2-position and the hydroxy alkane sulfonate having a sulfonate group at the 2-position based on the total amount of the component (A) and the component (B) was 20.1 mass %.

Production Example II-1: Production of C18 Component (A) and Component (B)

A C18 component (A) and component (B) were prepared from the C18 internal olefin (the content of the olefin raw material having a double bond at the 2-position was 31.3 mass %) prepared in Production Example C under the same conditions as in Production Example I.

The content of the component (A) based on the total amount of the resulting component (A) and component (B) was 20 mass %. The content of the remaining internal olefin raw material in the total amount of the component (A) and the component (B) was less than 100 ppm (less than the minimum limit of detection of GC), and the content of inorganic compounds was 0.9 mass %. The total content of the olefin sulfonate having a sulfonate group at the 2-position and the hydroxy alkane sulfonate having a sulfonate group at the 2-position based on the total amount of the component (A) and the component (B) was 21.4 mass %.

Production Example II-2: Production of C18 Component (A) and Component (B)

A C18 component (A) and component (B) were prepared from the C18 internal olefin (the content of the olefin raw material having a double bond at the 2-position was 13.8 mass %) prepared in Production Example D under the same conditions as in Production Example I.

The content of the component (A) based on the total amount of the resulting component (A) and component (B) was 20 mass %. The content of the remaining internal olefin raw material in the total amount of the component (A) and the component (B) was less than 100 ppm (less than the minimum limit of detection of GC), and the content of inorganic compounds was 1.0 mass %. The total content of the olefin sulfonate having a sulfonate group at the 2-position and the hydroxy alkane sulfonate having a sulfonate group at the 2-position based on the total amount of the component (A) and the component (B) was 9.1 mass %.

Production Example III-1: Production of C14 Component (A) and Component (B)

A C14 component (A) and component (B) were prepared from the C14 olefin raw material (the content of the olefin raw material having a double bond at the 2-position was 31.8 mass %) prepared in Production Example E under the same conditions as in Production Example I.

The content of the component (A) based on the total amount of the resulting component (A) and component (B) was 7 mass %. The content of the remaining olefin raw material in the total amount of the component (A) and the component (B) was 0 mass %, and the content of inorganic compounds was 0 mass %. The total content of the olefin sulfonate having a sulfonate group at the 2-position and the hydroxy alkane sulfonate having a sulfonate group at the 2-position based on the total amount of the component (A) and the component (B) was 21.7 mass %.

Production Example III-2: Production of C14 Component (A) and Component (B)

As Production Example III-2, a commercially available olefin sulfonate (Lipolan LB-440, manufactured by Lion Corporation) was used.

Production Example IV: Production of C16/C18 Component (A) and Component (B)

A C16/C18 component (A) and component (B) were obtained using the C16/C18 olefin raw material (the content of the olefin raw material having a double bond at the 2-position was 27.8 mass %) prepared in Production Example D as a starting raw material by the same method as in Production Example I. The content of the component (A) based on the total amount of the resulting component (A) and component (B) was 14 mass %. The content of the remaining olefin raw material in the total amount of the component (A) and the component (B) was less than 100 ppm (less than the minimum limit of detection of GC), and the content of inorganic compounds was 1.2 mass %. The total content of the olefin sulfonate having a sulfonate group at the 2-position and the hydroxy alkane sulfonate having a sulfonate group at the 2-position based on the total amount of the component (A) and the component (B) was 17.6 mass %.

Production Example V: Production of C14 Component (A) and Component (B)

The C14 component (A) and component (B) prepared in Production Example III-1 and a commercially available olefin sulfonate (Lipolan LB-440, manufactured by Lion Corporation) were mixed at a mass ratio of 45:55.

Table 1 shows the physical properties of the component (A) and the component (B) obtained in Production Examples I to V.

TABLE 1

| Production Example | | I-1 | I-2 | I-3 | II-1 | II-2 | III-1 | III-2 | IV | V |
|---|---|---|---|---|---|---|---|---|---|---|
| Olefin raw material | Content of olefin having double bond at 1-position (%) | 1.8 | 0.9 | 0.5 | 0.8 | 0.8 | 1.3 | — | 0.4 | — |
| | Content of olefin having double bond at 2-position (%) | 30.4 | 15.5 | 30.1 | 31.3 | 13.8 | 31.8 | — | 27.8 | — |

TABLE 1-continued

| Production Example | | I-1 | I-2 | I-3 | II-1 | II-2 | III-1 | III-2 | IV | V |
|---|---|---|---|---|---|---|---|---|---|---|
| Component (A) and component (B) | Number of carbon atoms | 16 | 16 | 16 | 18 | 18 | 14 | 14 | C16/C18*[1] | 14 |
| | Content of component (A) in total amount (mass %) | 10 | 16 | 44 | 20 | 20 | 7 | >80 | 14 | 57.9 |
| | Total content of hydroxy form and olefin form having sulfonate group at 1-position in total amount (mass %) | — | — | — | — | — | — | — | 2.9 | — |
| | Total content of hydroxy form and olefin form having sulfonate group at 2-position in total amount (mass %) | 20.3 | 9.3 | 20.1 | 21.4 | 9.1 | 21.7 | — | 17.6 | — |

*[1]Mass ratio of C16/C18 = 79.4/20.6

Examples 1 to 7 and Comparative Examples 1 to 3

Each composition was prepared according to the formulations shown in Table 2. In Comparative Example 2, sodium lauryl sulfate was used instead of the component (A) and component (B). Subsequently, the resulting compositions were evaluated for the plaque-dispersing effect according to the following test method.

The results are shown in Table 2.

«Plaque-Dispersing Effect Test»

1) Collection of Stimulating Saliva

Gum pellets included in Dentobuff Strip (OralCare Inc.) were chewed by healthy males in their twenties or thirties, and the saliva accumulated in their mouths was spit into Falcon tubes each time to thus collect saliva in Falcon tubes. Since there are individual differences in the bacteria in saliva, saliva collected from one healthy male was subjected to the plaque-dispersing effect test in all Examples and Comparative Examples.

2) Production of Plaque Model

The saliva collected in a Falcon tube was centrifugated at 3000 rpm, room temperature, for 10 minutes. The separated supernatant saliva was added with sucrose to prepare a 5 mass % sucrose solution, followed by stirring with a stirrer (Voltex, manufactured by Nippon Genetics Co., Ltd.) to prepare a plaque model test solution.

One surface of each HAp substrate (manufactured by Cosmo Bio, 1 cm square) was then mirror-polished with abrasive paper of 40 μm, 12 μm, and 3 μm, and the substrates were then immersed in 1N HCl for 1 minute for acid decalcification treatment. The HAp substrates after the treatment were washed with ion exchanged water, dried and put in a 24-well plate, and 1 mL of the plaque model test solution prepared above was added to each well. The plate was then stored in a plastic case together with a $CO_2$ pack to achieve anaerobic condition, and culturing was performed at 37° C. for 48 hours.

3) Evaluation of Plaque-Dispersing Effect

The saliva in the plate was sucked with a vacuum pump, and 1 mL of ion exchanged water was added thereto, followed by shaking for 5 minutes. The water was then sucked with a pump, and 1 mL of each of the compositions prepared in Examples and Comparative Examples was added to the respective wells, followed by shaking for 1 hour. The shaking was performed with a shaker (BioShake iQ (Waken B Tech Co., Ltd.)) under conditions of room temperature (25° C.) and 500 rpm.

Each composition was then sucked, and 1 mL of ion exchanged water was added thereto, followed by shaking for 5 minutes. This procedure was repeated twice. Subsequently, the water was sucked, and 750 μL of 0.1 mass % crystal violet (CV) solution was added thereto, followed by shaking for 15 minutes.

The CV stain solution was further sucked with a pump, and 1 mL of ion exchanged water was added thereto, followed by shaking for 5 minutes. This procedure was repeated twice. Subsequently, the water was sucked with a pump, and 500 mL of ethanol was added thereto, followed by pipetting. Subsequently, the extraction liquid was diluted 10 fold with ion exchanged water, and absorbance at $OD_{595\ nm}$ was measured with a microplate recorder (manufactured by Tecan Group Ltd., wavelength-variable absorbance microplate reader, SunriseRainbow Thermo).

The plaque residual rate (%) was calculated by the expression below using the absorbance $OD_{595\ nm}$ (initial value) when merely washed with ion exchanged water without using the resulting compositions above as the reference.

A smaller value of the resulting plaque residual rate means a higher plaque-dispersing effect.

Plaque residual rate (%)=[($OD_{595\ nm}$ when using the resulting composition above)/($OD_{595\ nm}$ when merely washed with ion exchanged water)]×100

TABLE 2

| | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|
| Production Example of component (A) and component (B) | III-1 | I-1 | I-2 | II-1 | II-2 | IV | I-3 | III-2 | — | V |

TABLE 2-continued

| | | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|---|
| Composition (mass %) | Total content of component (A) and component (B) | 0.5 | 0.5 | 0.5 | 0.5 | 0.5 | 0.5 | 0.5 | 0.5 | 0.5 | 0.5 |
| | Ion exchanged water | 99.5 | 99.5 | 99.5 | 99.5 | 99.5 | 99.5 | 99.5 | 99.5 | 99.5 | 99.5 |
| | Total | 100.0 | 100.0 | 100.0 | 100.0 | 100.0 | 100.0 | 100.0 | 100.0 | 100.0 | 100.0 |
| Plaque residual rate (%) | | 45 | 30 | 52 | 21 | 43 | 36 | 44 | 75 | 61 | 59 |

Examples 8 and 9 and Comparative Examples 4 to 7

Each oral composition was prepared according to the formulations shown in Table 3. Subsequently, each resulting oral composition was evaluated for discomfort and flavor according to the following test method.

The results are shown in Table 3.

«Evaluation of Discomfort and Flavor»

Specialized panelists held 20 mL of each resulting oral composition in the oral cavity for 40 seconds, spat it and then evaluated for discomfort such as harmfulness due to irritation like feeling of tingling of the gums or oral mucosa, and flavor according to the following evaluation criteria. The evaluation results were obtained through consultation.

A lower value means that the discomfort is suppressed and the flavor is good.

1: There was no feeling of irritation such as tingling at all and good flavor was shown.
2: There was slight feeling of irritation such as tingling.
3: There was feeling of irritation such as tingling.
4: There was strong feeling of irritation such as tingling.

TABLE 3

| Composition (mass %) | Example 8 | Example 9 | Comparative Example 4 | Comparative Example 5 | Comparative Example 6 | Comparative Example 7 |
|---|---|---|---|---|---|---|
| Component (A) and component (B) of Production Example II-1 | 1 | 3 | — | — | — | — |
| Sodium lauryl sulfate | — | — | 1 | 3 | — | — |
| Sodium tetradecenesulfonate | — | — | — | — | 1 | 3 |
| Sorbitol | 5 | 5 | 5 | 5 | 5 | 5 |
| Purified water | Balance | Balance | Balance | Balance | Balance | Balance |
| Total | 100 | 100 | 100 | 100 | 100 | 100 |
| Evaluation of discomfort and flavor | 1 | 1 | 2 | 4 | 3 | 4 |

What is claimed is:

1. An oral composition comprising the following components (A), (B), and (C):
   (A) an olefin sulfonate having 14 or more and 20 or less carbon atoms;
   (B) a hydroxy alkane sulfonate having 14 or more and 20 or less carbon atoms; and
   (C) sorbitol,
   wherein the content of the component (A) is 3 mass % or more and 50 mass % or less based on the total content of the component (A) and the component (B).

2. The oral composition according to claim 1, wherein the total content of an olefin sulfonate having a sulfonate group at the 2-position of the olefin chain in the component (A) and a hydroxy alkane sulfonate having a sulfonate group at the 2-position of the alkane chain in the component (B) is 5 mass % or more and 30 mass % or less based on the total content of the component (A) and the component (B).

3. The oral composition according to claim 1, wherein the total content of an olefin sulfonate having a sulfonate group at the 1-position of the olefin chain in the component (A) and a hydroxy alkane sulfonate having a sulfonate group at the 1-position of the alkane chain in the component (B) is 1 mass % or more and 20 mass % or less based on the total content of the component (A) and the component (B).

4. The oral composition according to claim 1, wherein the component (A) has 16 or more and 18 or less carbon atoms.

5. The oral composition according to claim 1, wherein the content of the component (C) is 2 mass % or more and 60 mass % or less.

6. The oral composition according to claim 1, wherein the content of the component (A) is 5 mass % or more and 45 mass % or less based on the total content of the component (A) and the component (B).

7. The oral composition according to claim 1, wherein the total content of the component (A) and the component (B) is 0.1 mass % or more and 10 mass % or less.

8. The oral composition according to claim 1, further comprising a surfactant (D) other than the component (A) and the component (B), wherein the component (D) is one or more selected from the group consisting of an anionic surfactant (D1) and a nonionic surfactant (D2).

9. The oral composition according to claim 8, wherein the anionic surfactant (D1) is one or more selected from the group consisting of sodium alkyl sulfate, sodium methyl lauroyl taurate, acyl glutamate, and acyl sarcosinate and the nonionic surfactant (D2) is one or more selected form the group consisting of polyoxyethylene hydrogenated castor oil, sucrose fatty acid ester, polyglycerol fatty acid ester, sorbitan fatty acid ester.

10. The oral composition according to claim 8, wherein the component (D) is the component (D1) and the content of the component (D1) is 0.05 mass % or more and 1.5 mass or less in total, or wherein the component (D) is the component (D2) and the content of the component (D2) is 0.1 mass % or more and 2 mass % or less in total.

11. The oral composition according to claim 1, which is a dentifrice composition that is toothpaste or powder dentifrice, or a liquid oral composition that is mouthwash or liquid dentifrice.

12. A method for producing the oral composition according to claim 1, comprising a step of preparing the component (A) and the component (B) through a step of sulfonating an olefin raw material having 14 or more and 20 or less carbon atoms to be used as a raw material of the component (A) and the component (B), followed by neutralization, hydrolysis, and subsequent purification of the resulting degradation product.

13. The method for producing the oral composition according to claim 12, wherein the step of purification comprises a step of adding a nonpolar solvent to the degradation product obtained by the hydrolysis and a step of separating an oil phase thereafter, and further comprises a step of extracting the component (A) and the component (B) from an aqueous phase after the separation.

14. The method for producing the oral composition according to claim 12, wherein the total content of an olefin having a double bond at the 2-position in an olefin raw material to be used as a raw material of the component (A) and the component (B) is 10 mass % or more and 50 mass % or less in total based on the total amount of the olefin raw material.

15. The method for producing the oral composition according to claim 13, wherein the step of adding a nonpolar solvent to the degradation product obtained by the hydrolysis is a step of dispersing the degradation product obtained by the hydrolysis in ethanol and then adding a nonpolar solvent thereto.

16. The method for producing the oral composition according to claim 13, wherein the nonpolar solvent is one or more selected from the group consisting of petroleum ether, hexane, and toluene.

17. A method for dispersing plaque, comprising applying the oral composition according to claim 1 to the oral cavity.

* * * * *